United States Patent [19]

Groen

[11] 4,343,796
[45] Aug. 10, 1982

[54] 2,3-BIS-HYDROXYBENZYL-DERIVATIVES

[75] Inventor: Marinus B. Groen, Schayk, Netherlands

[73] Assignee: AKZO NV, Oss, Netherlands

[21] Appl. No.: 272,727

[22] Filed: Jun. 11, 1981

[30] Foreign Application Priority Data

Jun. 24, 1980 [GB] United Kingdom ................ 8020688

[51] Int. Cl.$^3$ ................ A61K 31/695; C07C 69/773; A61K 31/35; C07C 69/017
[52] U.S. Cl. .................... 424/184; 424/278; 424/283; 424/308; 424/311; 424/341; 424/346; 556/486; 568/644; 568/729; 560/107; 560/108; 560/255; 542/427; 560/138; 560/100; 560/105; 549/214; 549/347; 549/415; 549/416
[58] Field of Search ............. 560/138, 255, 107, 108, 560/100, 105; 568/729, 644; 260/345.8 R, 345.9 R, 338; 556/486; 424/308, 311, 184, 341, 346, 278, 283; 542/427

[56] References Cited

PUBLICATIONS

*Chemical Abstracts*, vol. 76, 1972, p. 101, Abstract No. 87385v, Matsukura et al.
March, J., *Advanced Organic Chemistry: Reactions,*
*Mechanisms, and Structure,* McGraw-Hill, N.Y., 1968, pp. 696–697.

*Primary Examiner*—Natalie Trousof
*Assistant Examiner*—Frederick W. Pepper
*Attorney, Agent, or Firm*—Abelman, Frayne & Rezac

[57] ABSTRACT

The invention relates to compounds of the formula:

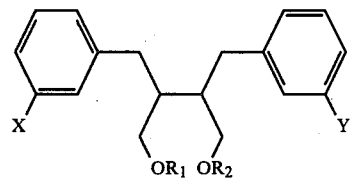

in which
$R_1$ and $R_2$ are the same or different groups selected from hydrogen or acyl or
$R_1$ and $R_2$ together may represent an acetal group, and
X and Y are the same or different groups selected from hydroxy, an etherified hydroxy and an esterified hydroxy group,
having valuable lipid lowering, anti-inflammatory and immuno-modulating properties.

4 Claims, No Drawings

2,3-BIS-HYDROXYBENZYL-DERIVATIVES

The invention relates to bis-hydroxybenzyl-derivatives, to processes for their preparation and to pharmaceutical compositions containing same.

More particularly the invention relates to compounds of the formula:

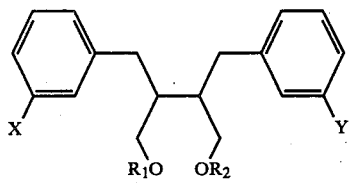
(I)

in which X and Y may be the same or different groups selected from hydroxy, an etherified hydroxy and an esterified hydroxy group, and $R_1$ and $R_2$ represent hydrogen or acyl, or together an acetal group.

The compounds of formula I possess valuable lipid-lowering and anti-inflammatory activities and are potent immuno-modulators with low toxicity. They enhance cell-mediated immunity, stimulate the action of phagocytic cells and inhibit complement. They can generate a cell killing activity against foreign cells, such as cancer cells. They are also useful for the control of pregnancy, as they can modify tolerance of foetal tissue.

A convenient starting product for the preparation of the present compounds, is a compound of the general formula:

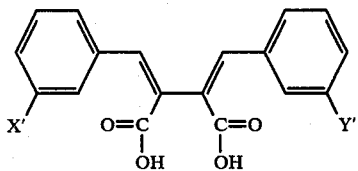
II or an ester thereof, in which $X^1$ and $Y^1$ represent a free or etherified hydroxyl group.

This starting product of formula II may be prepared by means of a "double" Stobbe condensation using a di-ester of succininc acid and benzaldehyde, that is provided with a protected hydroxyl group in meta-position. This condensation is carried out in the presence of a strong base and yields the compound II, where necessary after deprotection of the hydroxyl group and/or esterification of the carboxyl group(s).

The above compound of formula II may be reduced to a compound of formula I preferably with the aid of a complex metalhydride such as LiAlH$_4$ or NaAlH$_2$-((OCH$_2$CH$_2$OCH$_3$)$_2$. Both double bonds and carboxylic acid moieties are reduced simultaneously in this reduction. This reduction yields a mixture of the erythro and threo stereo-isomers, which isomers may be separated by wellknown methods such as crystallisation or column chromatography.

A stereospecific method for preparing compounds of formula I consists of a catalytic hydrogenation of the compound II followed by a reduction of the compound thus obtained by means of a complex metalhydride. The said catalytic hydrogenation, e.g. H$_2$/Pd/C, whereby (only) the double bonds of II are reduced, runs in a stereospecific manner in that mainly the erythro form of a compound of the general formula:

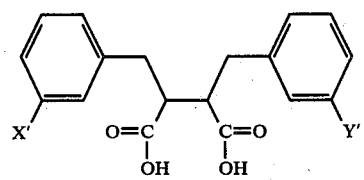
III or an ester thereof, in which $X^1$ and $Y^1$ have the aforesaid meanings, is obtained.

In a subsequent step the compound III may be reduced with a complex metalhydride in the manner as described before to obtain a compound I, which is mainly in the erythro form.

Another method for the preparation of the compounds I consists of a reduction of the lactone of the formula:

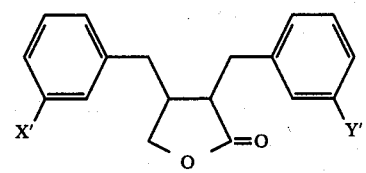
IV or a reduction of the "open" isomer of this lactone, viz. a compound of the formula:

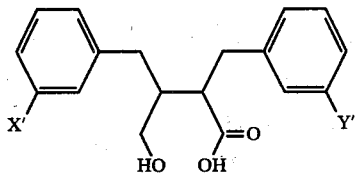
IVA or an ester thereof, in which $X^1$ and $Y^1$ have the meanings indicated above.

The reduction of a compound of the formulae IV or IVA is carried out in the usual manner, preferably by complex metalhydrides, such as LiAlH$_4$, NaAlH$_4$ or NaAlH$_2$(OCH$_2$CH$_2$OCH$_3$)$_2$.

Compounds of formula IV and IVA are described already in our copending British patent application No. 80.13.040. A method for the preparation of these compounds is briefly discussed in the flow sheet on the next page.

The compounds of the invention obtained by one of the methods described above may additionally be acylated at one or more free hydroxy groups.

In the usual acylation process, using the acylhalide or anhydride as acylating agent, the phenolic hydroxy groups will be acylated first, then followed by acylation of the aliphatic hydroxy groups.

If only an acylation of the aliphatic hydroxy groups is desired, the phenolic hydroxy groups should suitably be protected prior to the acylation and afterwards be deprotected, or, alternatively, the phenolic ester groups may selectively be removed from the fully acylated product.

Flow sheet

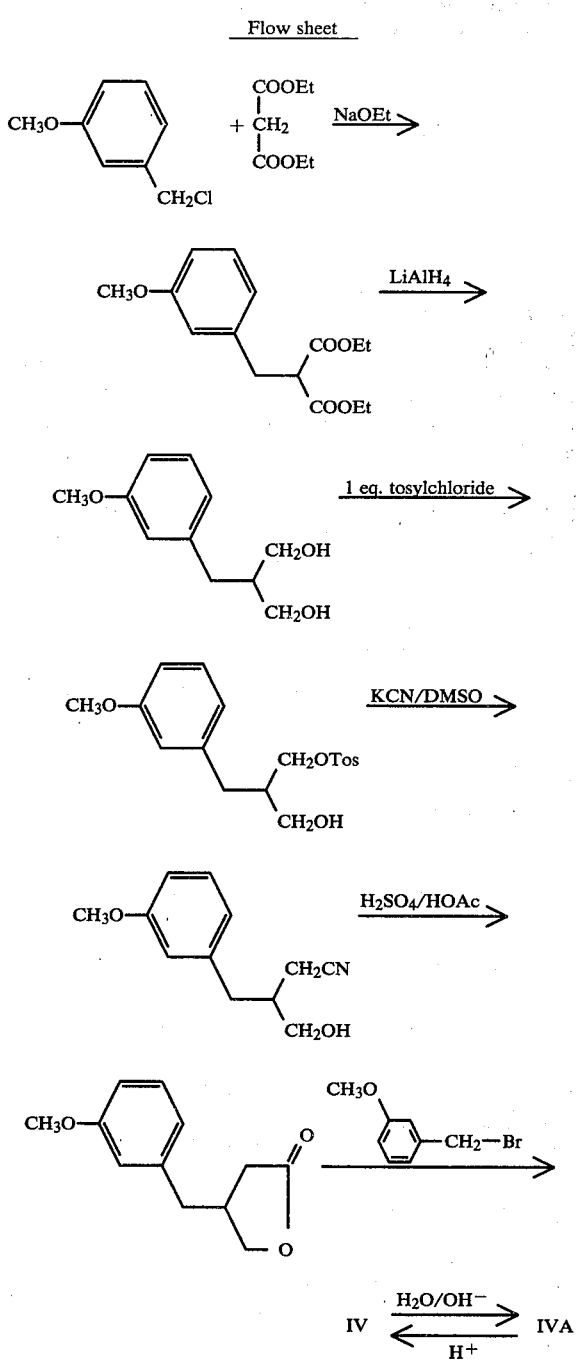

An etherified hydroxy group is usually a hydrocarbon-oxy radical with 1 to 10 carbon atoms, such as methoxy, ethoxy, allyloxy, propyloxy isopropyloxy, butoxy, hexyloxy and benzyloxy, but also other ether moieties are possible such as a trimethylsilyoxy and tetrahydropyranyl-2-oxy group.

Said etherified hydroxy group is preferably already present in the starting products defined before (II, III, IV, IVA). If, however, a free hydroxy group is desired in the endproduct of formula I, it is of course possible to convert said ether moiety into the free hydroxy moiety by methods in actual use or described in the literature. For example, a methoxy group can easily be converted into a hydroxy group by the action of borontribromide.

An esterified hydroxy group (as used in the definition of X and Y) is usually an acyloxy group in which the acyl group is derived from an aliphatic carboxylic acid with 1 to 6 carbon atoms or an aromatic carboxylic acid with 7 to 10 carbon atoms, such as acetic acid, propionic acid, butyric acid, pentanoic acid, hexanoic acid, benzoic acid, phenyl acetic acid, phenyl propionic acid and cinnamic acid.

The acyl group in the definition of $R_1$ and $R_2$ has a similar meaning as defined above.

The compounds of formula I can generally be obtained in two diastereo-isomeric forms, namely in erythro or threo form. In general, each of these diastereo-isomers can exist in two enantiomeric forms having the R,R and S,S or R,S and S,R configuration at the asymmetric centres respectively. However, in the special case of a compound I in which $X=Y$ and $R_1=R_2$, the isomers with R,S and S,R configurations become identical and optically inactive (meso form), so that the total number of stereo-isomers is reduced to three.

Both diastereo-isomeric forms as well as the optically active enantiomers of formula I are compounds according to this invention. The diastereo-isomers may, if necessary, be separated in the usual manner by e.g. fractional crystallization, column chromatography, preparative thin layer chromatography or counter current distribution.

A racemic mixture of formula I may be separated into the separate optical enantiomers of formula I in the usual manner e.g. with the aid of an optically active base.

The compounds according to the invention can be processed to customary liquid or solid pharmaceutical preparations, for example to sugar-coated pills, tablets, suppositories and solutions also for injections. The customary excipients and diluents are used for this purpose.

The oral single dose ranges from 0.01–100 mg/kg body weight, the oral daily dose ranges from 0.03 to 300 mg/kg body weight. The parenteral single dose ranges from 1 γ to 10 mg/kg body weight. The daily dose is about the threefold quantity of this single dose. As anti-inflammatory drug, the compound of the invention may also be incorporated in an ointment, gel or paste for local application. Preferably the drug is present in the ointment, gel or paste in an amount of 0.01 up to 2.5% of the total composition.

Preferred compounds of the invention are the meso or erythro isomers of formula I, in which X and Y are hydroxy and $R_1$ and $R_2$ hydrogen, and the corresponding mono, di, tri or tetra acylated derivatives thereof. An acylated phenolic hydroxy group, e.g. acetylated or benzoylated, is hereby particularly preferred.

EXAMPLE 1 d,1 2,3-bis[(3-hydroxyphenyl)methyl]-1,4-butane diol

A mixture of 0.3 g (1 mmol) trans-(±)-3,4-[(3-hydroxyphenyl)methyl]-2-(3H) furanone and 0.1 g lithiumaluminiumhydride in 10 ml of dry tetrahydrofuran (THF) was stirred for 2 hours at ambient temperature. The reaction mixture was acidified with 2 n HCl and extracted with ethyl acetate.

The ethyl acetate extracts were subsequently dried and evaporated. The oily residue was stirred in chloroform whereby the product crystallized.

Yield: 0.22 g; melting point 173°–175° C.

EXAMPLE 2

In the same manner as described in Example 1, the optically active lactone trans(−)-3,4-[(3-hydroxyphenyl)methyl]-2-(3H)-furanone, $[\alpha]_D^{20} = -38.4°$ C. (CHCl$_3$), was converted into the optically active diol.

Yield: oil, $[\alpha]_D^{20} = -18°$ C. (acetone).

EXAMPLE 3

In the same manner as described in Example 1, cis-(±)-3,4-[(3-hydroxyphenyl)methyl]-2-(3H)-furanone was reduced, yielding after chromatografic purification (silica gel column, solvent system: ethylacetate) the optically inactive meso-3,4-[(3-hydroxyphenyl)methyl]-1,4-butane diol as a viscous oil, which crystallized from chloroform, m.p. 122°–125° C.

EXAMPLE 4

Meso-2,3-bis-[(3-hydroxyphenyl)methyl]-1,4-butane diol

A mixture of 8.16 g (0.06 mol) m-methoxybenzaldehyde 4.3 g diethylsuccinate, 3.4-g sodiumethoxide and 35 ml dry ether was stirred for 24 hours at room temperature. Water was added to the reaction mixture, whereafter the mixture was extracted with dichloromethane. The water layer was acidified with HCl and subsequently extracted with ethylacetate. The organic extracts were dried and evaporated yielding 1.4 g of an oily product, crude 2,3-bis-(3-methoxybenzylidene)succinic acid.

This crude product was hydrogenated in acetic acid for 3 days at room temperature, using 0.14 g 5% palladium on carbon as catalyst. The mixture was filtered, whereafter the filtrate was evaporated.

The oily residue was dissolved in ether after which a solution of diazomethane in ether (app. 1 mole) was added. The mixture was stirred for 2 hours at room temperature and then evaporated.

The residue was chromatographed over a silica gel column using hexane:ethylacetate (8:2) as the solvent system.

Yield: oily residue, 1.0 g.

Product: meso-dimethyl-2,3-bis-[(3-methoxyphenyl)methyl]succinate.

This oily residue obtained was dissolved in 10 ml of dry dichloromethane and cooled down to −70° C., after which 1 ml borontribromide was added. The mixture was stirred for half an hour, and then slowly heated up to about 0° C. At this temperature the mixture was further stirred for another 15 minutes.

After the addition of water the reaction mixture was extracted with ethylacetate. The combined extracts were subsequently dried and evaporated. The residue was dissolved in 30 ml dry THF, after which 0.4 g lithiumaluminium was added. The mixture was stirred for 2 hours and then acidified with 2 N HCl, after which it was extracted with ethylacetate.

The combined extracts were dried and evaporated and the residue chromatographed over silicagel using ethylacetate as solvent.

Yield: 0.44 g, m.p. 120°–123° C.

Rf in hexane:acetone (1:1)=0.19 on SiO$_2$.

EXAMPLE 5 d,1-2,3-bis[(3-acetoxyphenyl)methyl]1,4-butane diol 1,4-diacetate

A mixture of 0.3 g d,1-2,3-bis[(3-hydroxyphenyl)methyl]-1,4-butane diol, 3 ml acetic anhydride and 1 ml pyridine was stirred at room temperature for 24 hours after which water was added.

The mixture was then extracted with dichloromethane.

The combined extracts were subsequently washed with 2 N HCl and sodium bicarbonate solution (10%) in water, after which they were dried and evaporated.

The residue was a colourless oil; yield 0.47 g.

Rf in hexane:ethylacetate (3:2)=0.30 on SiO$_2$.

EXAMPLE 6

In an analogous manner as described in Example 5 the following compounds were prepared:

(−)2,3-bis[(3-acetoxyphenyl)methyl]-1,4-butane diol-1,4-diacetate;

meso 2,3-bis[(3-acetoxyphenyl)methyl]-1,4-butane diol-1,4-diacetate;

d,1-2,3-bis[(3-propionyloxyphenyl)methyl]-1,4-butane diol-1,4-dipropionate.

EXAMPLE 7 d,1-2,3-bis[(3-benzoyloxyphenyl)methyl]-1,4-butane diol 0.42 g (3 mmol) of benzoylchloride was added in small portions to a solution of 0.3 g (1 mmol) d,1-2,3-bis[(3-hydroxyphenyl)methyl]-1,4-butane diol in 10 ml 1 N NaOH, while vigorously stirring.

The reaction mixture was extracted with ethylacetate. The combined extracts were dried and evaporated, after which the residue was chromatographed over a silica gel column using the solvent system hexane:ethylacetate (1:1).

Yield: 0.4 g colourless oil.

Rf in hexane:ethylacetate

EXAMPLE 8 meso-2,3-bis[(3-hydroxyphenyl)methyl]-1,4-butane diol acetonide.

0.1 g Of the diol obtained in Example 3 is refluxed in acetone for 1 hour after which the mixture is cooled down.

I claim:

1. A compound of the formula

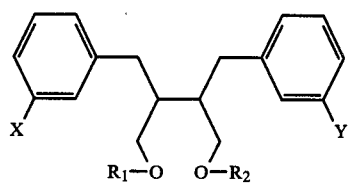

wherein X and Y are the same or different and are selected from the group consisting of hydroxy, alkoxy having 1 to 10 carbon atoms, trimethylsilyloxy, tetrahydropyranyl-2-oxy, (C$_{1-6}$)-alkanoyloxy, (C$_{7-10}$)-aroyloxy, (C$_{7-10}$)-aralkanoyloxy, and a (C$_{7-10}$)-aralkenoyloxy R$_1$ and R$_2$ are the same or different and are selected from the group consisting of hydrogen, (C$_{1-6}$)-alkanoyl, (C$_{7-10}$)-aroyl, (C$_{7-10}$)-aralkanoyl, and a (C$_{7-10}$)-aralkenoyl, and R$_1$ and R$_2$, when taken together with the oxygen atoms to which they are attached, represent an acetal group.

2. A compound according to claim 1 of the formula:

3. A compound according to claim 1 of the formula:
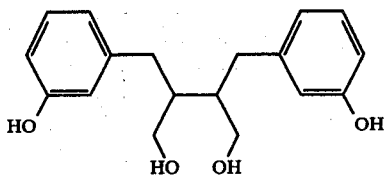
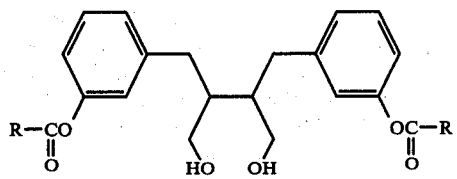
in which R represents methyl or phenyl, or a diacetyl or di-propionyl derivative thereof.
4. An anti-inflammatory pharmaceutical composition containing, as active ingredient, an anti-inflammatory effective amount of a compound according to claim 1 and a pharmaceutically acceptable carrier or diluent.